US012239289B2

(12) United States Patent
Shear et al.

(10) Patent No.: US 12,239,289 B2
(45) Date of Patent: Mar. 4, 2025

(54) ENDOSCOPE INSTRUMENTATION DRIVE SYSTEM

(71) Applicants: William Shear, Amarillo, TX (US); Alexander G Sammons, Fairfax Station, VA (US)

(72) Inventors: William Shear, Amarillo, TX (US); Alexander G Sammons, Fairfax Station, VA (US)

(*) Notice: Subject to any disclaimer, the term of this patent is extended or adjusted under 35 U.S.C. 154(b) by 4 days.

(21) Appl. No.: 18/048,785

(22) Filed: Oct. 21, 2022

(65) Prior Publication Data

US 2023/0055852 A1 Feb. 23, 2023

Related U.S. Application Data

(63) Continuation of application No. 16/853,746, filed on Apr. 20, 2020, now abandoned.

(51) Int. Cl.
*A61B 1/00* (2006.01)
*A61B 1/06* (2006.01)

(52) U.S. Cl.
CPC ........ *A61B 1/0016* (2013.01); *A61B 1/00006* (2013.01); *A61B 1/00027* (2013.01); *A61B 1/00055* (2013.01); *A61B 1/00121* (2013.01); *A61B 1/00133* (2013.01); *A61B 1/0676* (2013.01); *A61B 2562/02* (2013.01)

(58) Field of Classification Search
CPC .............. A61B 1/0016; A61B 1/00027; A61B 1/00055; A61B 1/00121; A61B 1/00133; A61B 1/00034; A61B 1/00059; A61B 5/064; A61B 2090/061; A61B 1/00137
See application file for complete search history.

(56) References Cited

U.S. PATENT DOCUMENTS

| | | |
|---|---|---|
| 2003/0040737 A1 | 2/2003 | Merril |
| 2006/0161043 A1 | 7/2006 | Neumann |
| 2007/0078301 A1 | 4/2007 | Kura |
| 2007/0299305 A1 | 12/2007 | Murakami |
| 2008/0146875 A1* | 6/2008 | Noguchi ............ G02B 23/2484 600/117 |
| 2008/0319260 A1* | 12/2008 | Murakami ............. A61B 90/98 600/106 |
| 2011/0319708 A1 | 12/2011 | Shapiro |
| 2019/0174996 A1 | 2/2019 | Yamada |

FOREIGN PATENT DOCUMENTS

WO 2017023901 A1 2/2017

* cited by examiner

*Primary Examiner* — Aaron B Fairchild
(74) *Attorney, Agent, or Firm* — Shannon Warren

(57) ABSTRACT

An instrument drive system configured to attach to an instrument channel of an endoscope assembly and manage a relative feed position of an instrument using two drive wheels and a device application in a controller. The instrument drive system is attached directly to the instrument channel of the endoscope assembly. operation of the instrument drive system is proximate to the endoscope assembly and an inputs-controls and a deflection control thereof.

14 Claims, 6 Drawing Sheets

ENDOSCOPE INSTRUMENTATION DRIVE SYSTEM

CROSS-REFERENCE TO RELATED APPLICATIONS

This application is a continuation-in-part of U.S. Ser. No. 16/853,746 filed 2020 Apr. 20, which in turn claims benefit to U.S. 62/836,188 filed 2019 Apr. 19. Both applications are hereby incorporated by reference.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

No prior art is known to the Applicant.

BRIEF SUMMARY OF THE INVENTION

An instrument drive system configured to attach to an instrument channel of an endoscope assembly and manage a relative feed position of an instrument using two drive wheels and a device application in a controller. Said instrument drive system is attached directly to said instrument channel of said endoscope assembly. operation of said instrument drive system is proximate to said endoscope assembly and an inputs-controls and a deflection control thereof.

Said instrument drive system configured to attach to said instrument channel of said endoscope assembly and manage a relative feed position of said instrument using said two drive wheels and said device application in said controller. Said instrument drive system is configured to work in conjunction with said instrument comprising a plurality of machine-readable signatures. Said instrument drive system further comprises an optical data reader configured to read a portion of said plurality of machine-readable signatures as said instrument is feed into and removed from said instrument drive system. Said device application is configured to decode said plurality of machine-readable signatures and thereby determine a relative feed position of said instrument within said instrument drive system and said endoscope assembly.

DETAILED DESCRIPTION OF THE INVENTION

The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
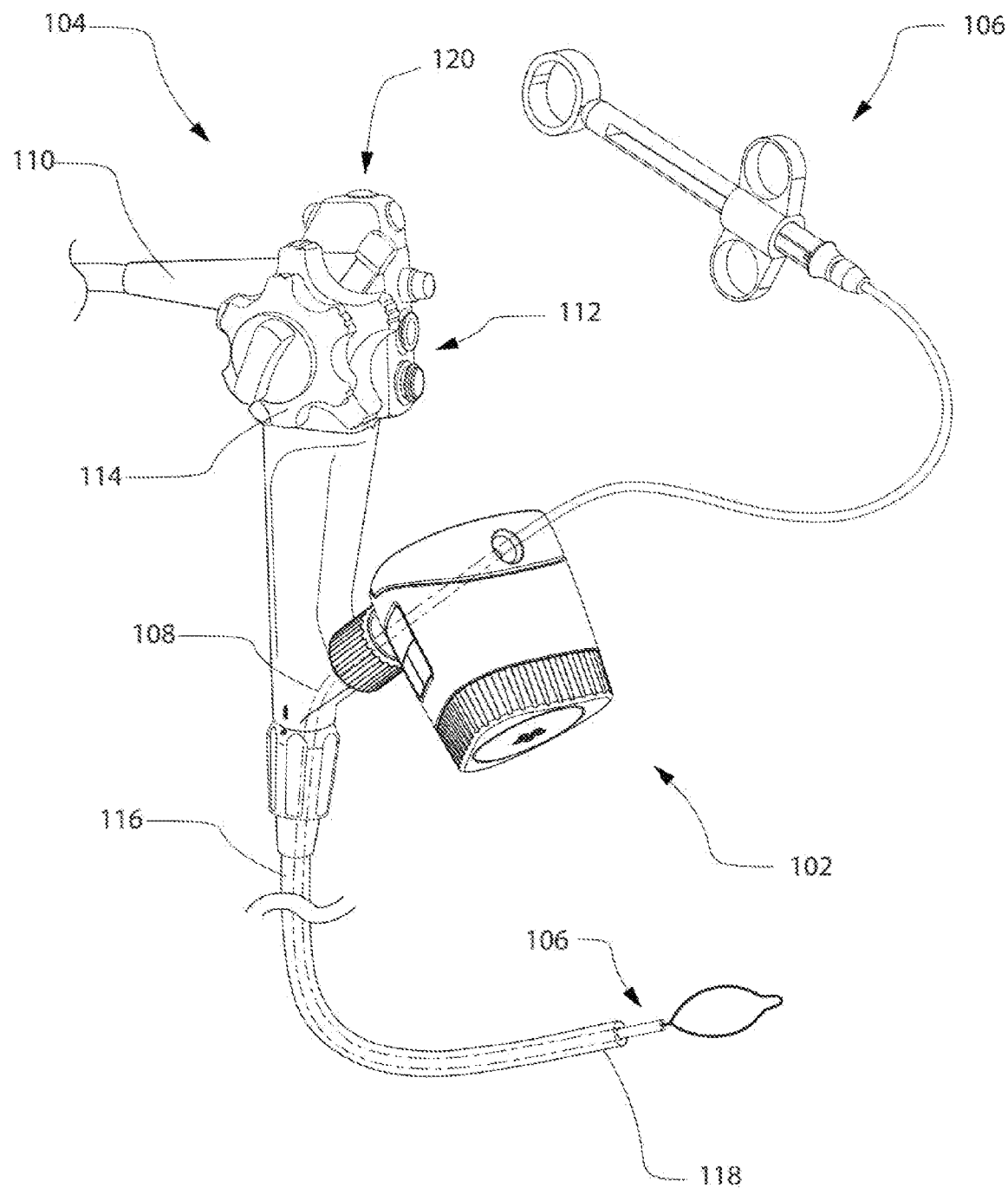
FIG. 1 illustrates a perspective view of an endoscope assembly 104 with an instrument drive system 102 and an instrument 106.

FIG. 1 illustrates a perspective view of an endoscope assembly 104 with an instrument drive system 102 and an instrument 106.

In one embodiment, said instrument drive system 102 can be adapted for feeding said instrument 106 into an instrument channel 108.

As is known in the art, said endoscope assembly 104 can comprise an inputs-line 110 with an inputs-controls 112 which can provide gasses, fluids such as water, optical fiber and/or suction, according to the needs at hand. Said endoscope assembly 104 can comprise a deflection control 114, a flexible shaft 116 having a distal end 118, and an optical viewer 120.

In one embodiment, said instrument 106 can comprise cameras, catheters, snare, forceps, or similar instruments as used in the medical industry, as is known in the art. For discussion purposes, it is noted that said instrument drive system 102 can be adapted to drive one or more different instruments.

Said endoscope assembly 104 are well known in the art, said instrument drive system 102 can be useful to improve said endoscope assembly 104 and outcomes for medical treatments. Said optical viewer 120 can comprise a digital output to a monitor or an optical eye piece. Said instrument channel 108 can comprise a channel for inserting said instrument 106 into and through said flexible shaft 116.

Figure 2A:
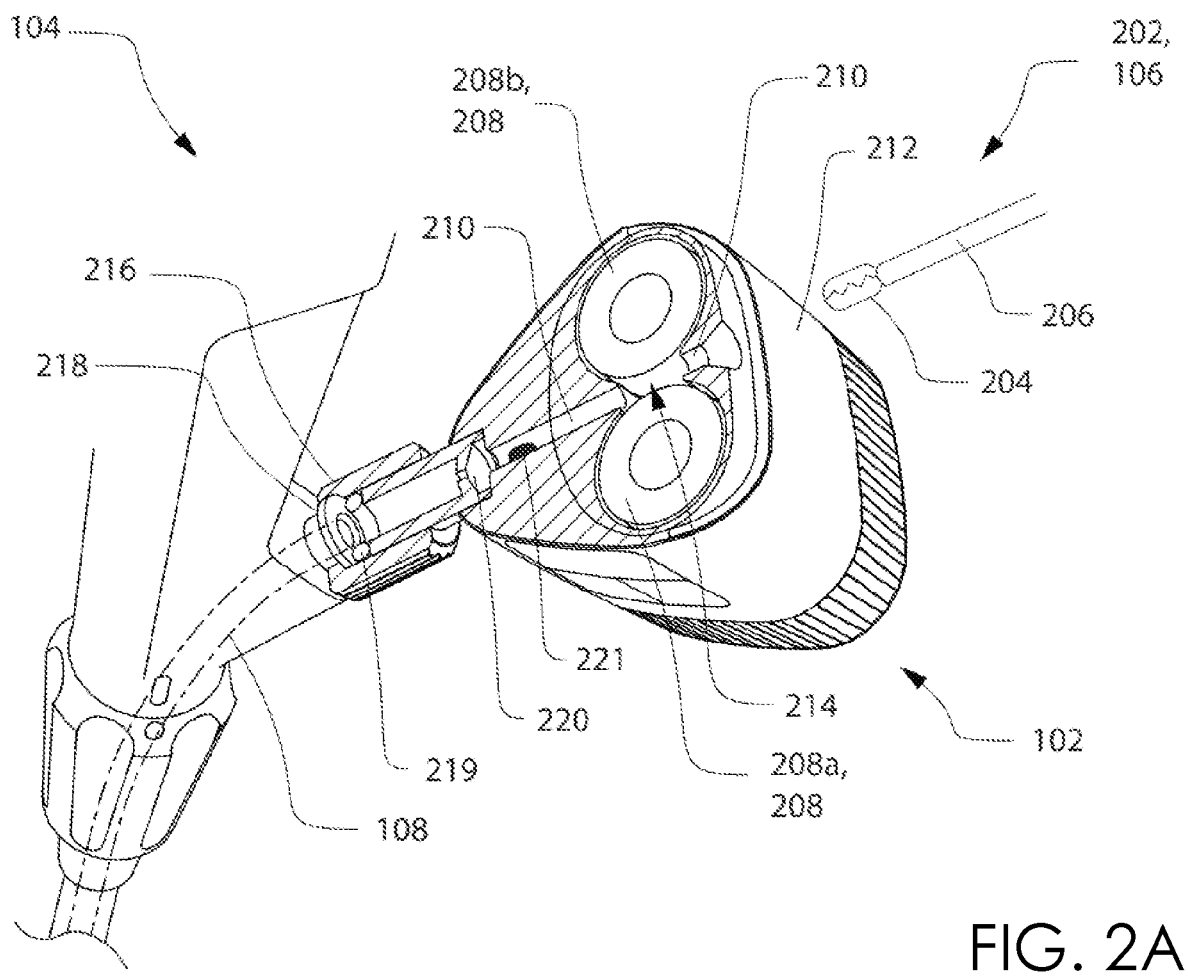
FIGS. 2A and 2B illustrate a first and second cutaway perspective view of said instrument drive system 102.
Figure 2B:
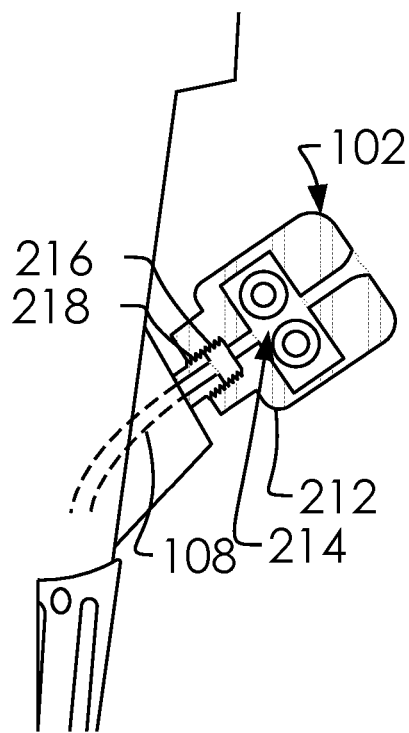

FIGS. 2A and 2B illustrate a first and second cutaway perspective view of said instrument drive system 102.

Said instrument 106 can comprise a first instrument 202 having a distal instrument 204, and a shaft 206.

Said instrument drive system 102 can comprise two drive wheels 208 (which comprise a first drive wheel 208a, and a second drive wheel 208b), a working channel 210, an optical data reader 221, a body 212, and a drive gap 214.

In one embodiment, said working channel 210 can receive and release a portion of said instrument 106.

In one embodiment, said instrument drive system 102 can comprise a female locking coupling 216 for mounting to a male locking coupling 218 of said instrument channel 108.

In one embodiment, said female locking coupling 216 can comprise a port gasket 219 that can form a hermetic seal between said female locking coupling 216 and said male locking coupling 218 of said instrument channel 108.

In one embodiment, said female locking coupling 216 can comprise a shaft gasket 220 that can form a hermetic seal between said female locking coupling 216 and said shaft 206.

Figure 3A:
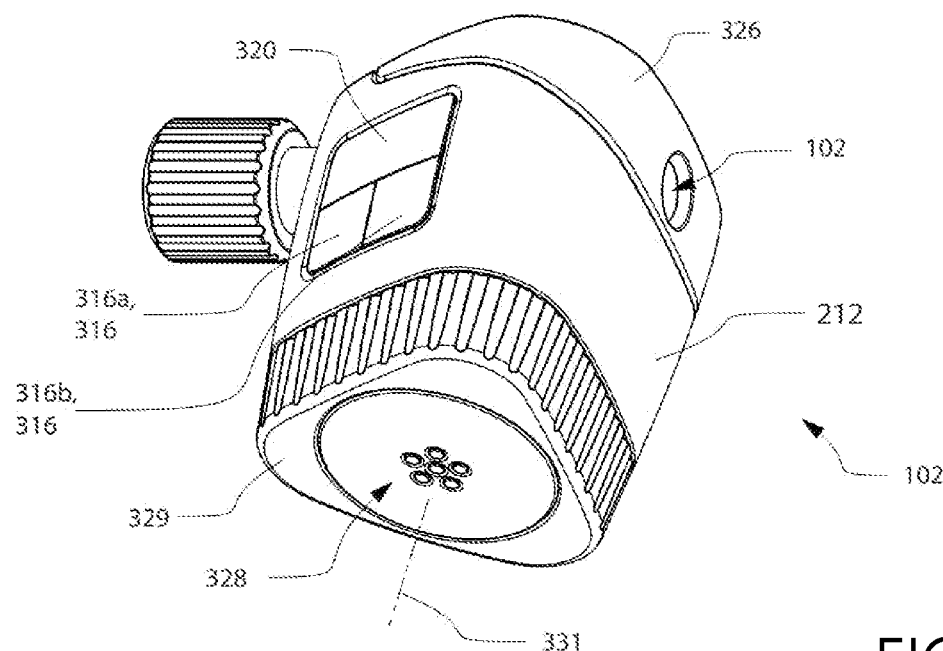
FIGS. 3A and 3B illustrate two perspective views of said instrument drive system 102.
Figure 3B:
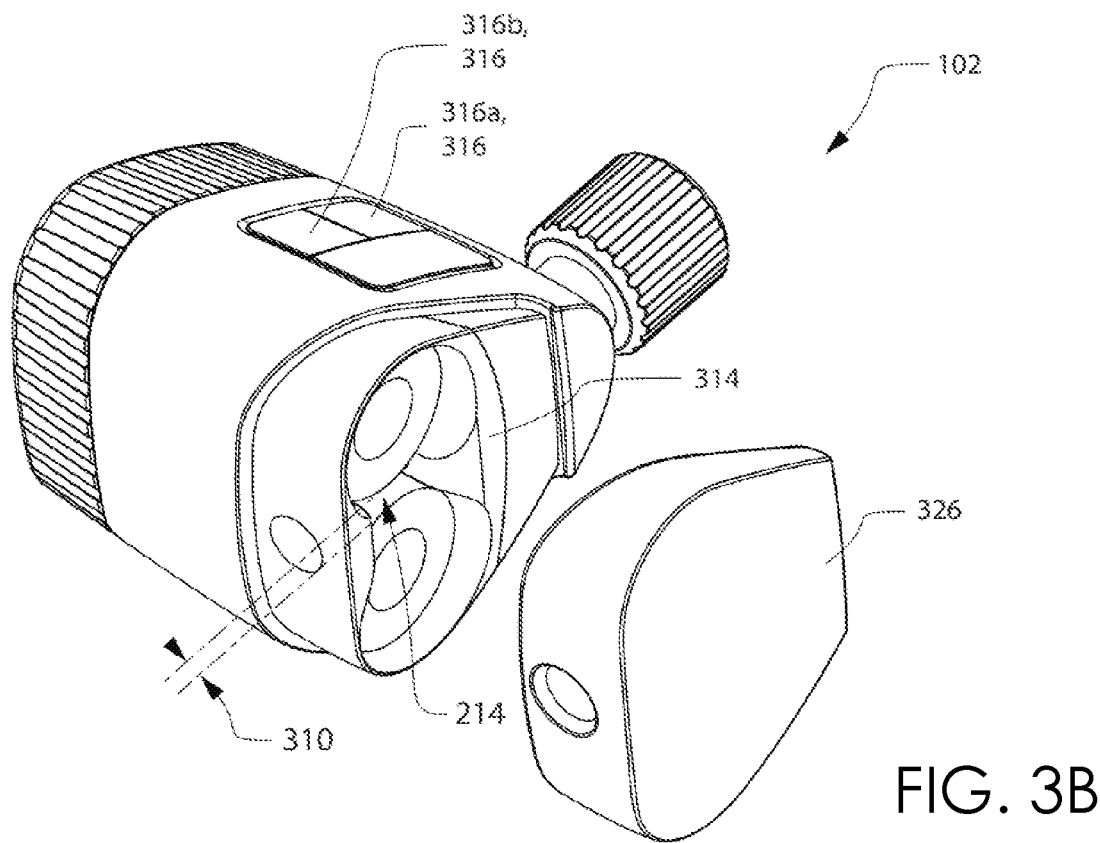

FIGS. 3A and 3B illustrate two perspective views of said instrument drive system 102.

Said instrument drive system 102 can comprise said two drive wheels 208. In one embodiment, said two drive wheels 208 can be removeable, rechargeable and adjustable, as discussed herein. In one embodiment, said two drive wheels 208 can be located inside of said body 212 and under a cover 326. In one embodiment, said cover 326 can be clear to monitor the status of said shaft 206, said two drive wheels 208, said working channel 210, and said drive gap 214. In one embodiment, said cover 326 can be removeable to address any issues within said body 212.

In one embodiment, said two drive wheels 208 can comprise an adjustable tensioner 302 to allow for fine tuning of instrumentation feed speed, and a clutch-brake assembly 304 which can allow for decoupling of a motor drive 306 and/or a brake 308. Said instrument drive system 102 can further comprise a battery 312 for operating said two drive wheels 208, one or more direction buttons 316 (which can comprise a forward direction button 316a and a reverse direction button 316b). said one or more direction buttons 316 can be used to switch the polarity of said motor drive 306 for insertion/removal of said instrument 106.

In one embodiment, said instrument drive system 102 can comprise a control knob 329 rotatably mounted to said body 212. Said control knob 329 can be used to switch the polarity of said motor drive 306 for insertion/removal of said instrument 106 by rotating said control knob 329 clockwise and counterclockwise with respect to a control axis 331. Said control knob 329 can further control the desired speed of insertion/removal of said instrument 106. In one embodiment, the speed of insertion/removal can be linearly or non-linearly related to the angle of rotation of said control knob 329.

In one embodiment, said drive gap 214 can be adjustable to one or more widths 310 to accommodate different diameters for said instrument 106.

Said instrument drive system 102 can further comprise a battery level monitor 318 and an indicator display 320. Thus, said instrument drive system 102 can be configured to monitor the status of said battery 312, and indicate a healthy battery with a first signal (such as a green light, a flashing light, or not light at all on said indicator display 320) or an unhealthy battery with a second signal (such as a red or yellow light on said indicator display 320). Furthermore, said instrument drive system 102 can configure said indicator display 320 to display characters, symbols and animations representative of the various alarms and modes of operation of said instrument drive system 102.

In one embodiment, said instrument drive system 102 can comprise a charging and communication port 328. Wherein, said charging and communication port 328 can receive a power plug for charging/quick charging said battery 312 from an external power supply/charging cradle, as is known in the art. In one embodiment, said instrument drive system 102 may not include said battery 312 or said battery level monitor 318; wherein, said charging and communication port 328 can be more correctly known as a power input port in that case. In one embodiment, said two drive wheels 208 can comprise a sealed system which can be rechargeable and/or able to be draw corded power from the tower, as is known in the art.

Said motor drive 306 can require adequate power, speed, and forward/reverse torque to accomplish the task according to the needs at hand. One design objective is a light weight, small relative unit size that will not upset ergonomics and balance of said endoscope assembly 104.

Figures 4A, 4B:
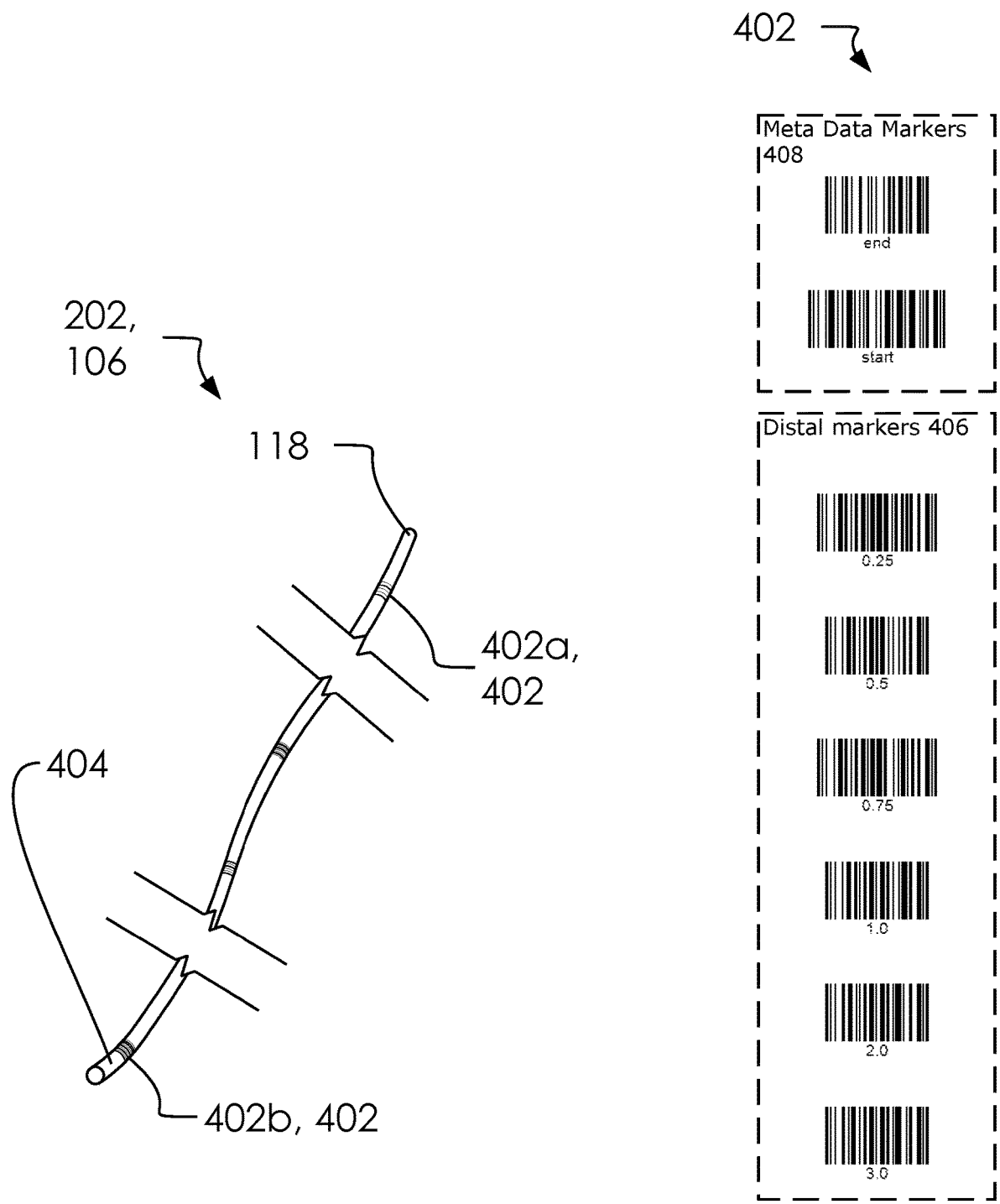
FIGS. 4A and 4B illustrate a perspective overview of said instrument 106 with a plurality of machine-readable signatures 402, and a selection of samples of said plurality of machine-readable signatures 402.

FIGS. 4A and 4B illustrate a perspective overview of said instrument 106 with a plurality of machine-readable signatures 402, and a selection of samples of said plurality of machine-readable signatures 402.

Said plurality of machine-readable signatures 402 can comprise a foil band or other optically unique signature at both ends of said instrument 106.

In one embodiment, said plurality of machine-readable signatures 402 can comprise one or more meta data markers 408 such a first optical signature 402a at said distal end 118 of said instrument 106 and a second optical signature 402b at a proximal end 404 of said instrument 106. In one embodiment, a portion of said one or more meta data markers 408 can disclose a total length, a diameter, a rigidity of said instrument 106.

In one embodiment, one or more distal markers 406 can be affixed to said instrument 106 to determine a location along said instrument 106. In one embodiment, said one or more distal markers 406 can be at pre-determined distances from one another.

In one embodiment, said instrument drive system 102 can be configured to read said plurality of machine-readable signatures 402 using said optical data reader 221.

Figure 5:
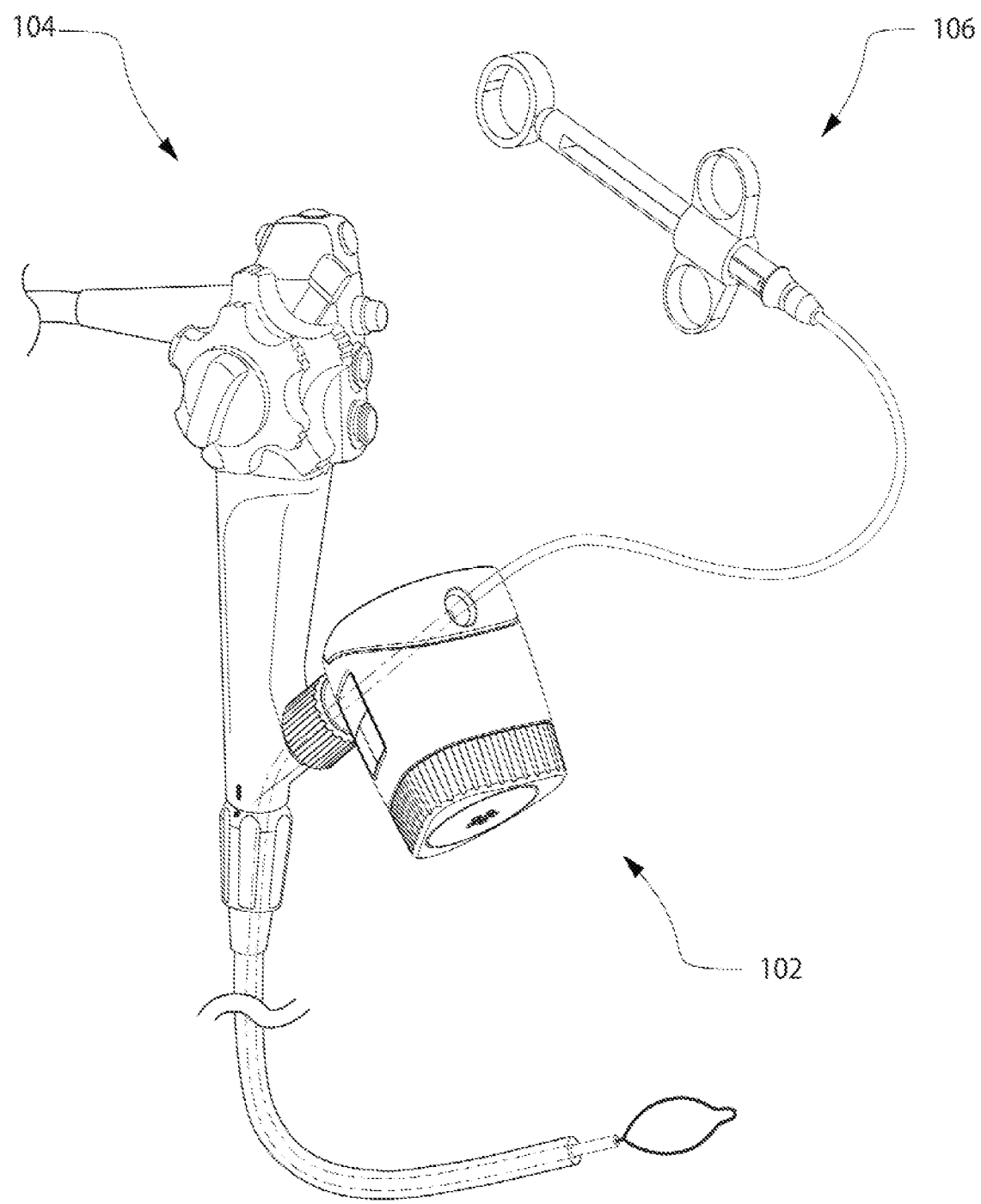
FIG. 5 illustrates a perspective overview of said endoscope assembly 104, said instrument drive system 102 and said instrument 106.

FIG. 5 illustrates a perspective overview of said endoscope assembly 104, said instrument drive system 102 and said instrument 106.

One advantage of said instrument drive system 102 can comprise the attachment of said instrument drive system 102 directly to said instrument channel 108 of said endoscope assembly 104. Wherein, operation of said instrument drive system 102 can be proximate to said endoscope assembly 104 and said inputs-controls 112 and said deflection control 114 thereof.

Figure 6:
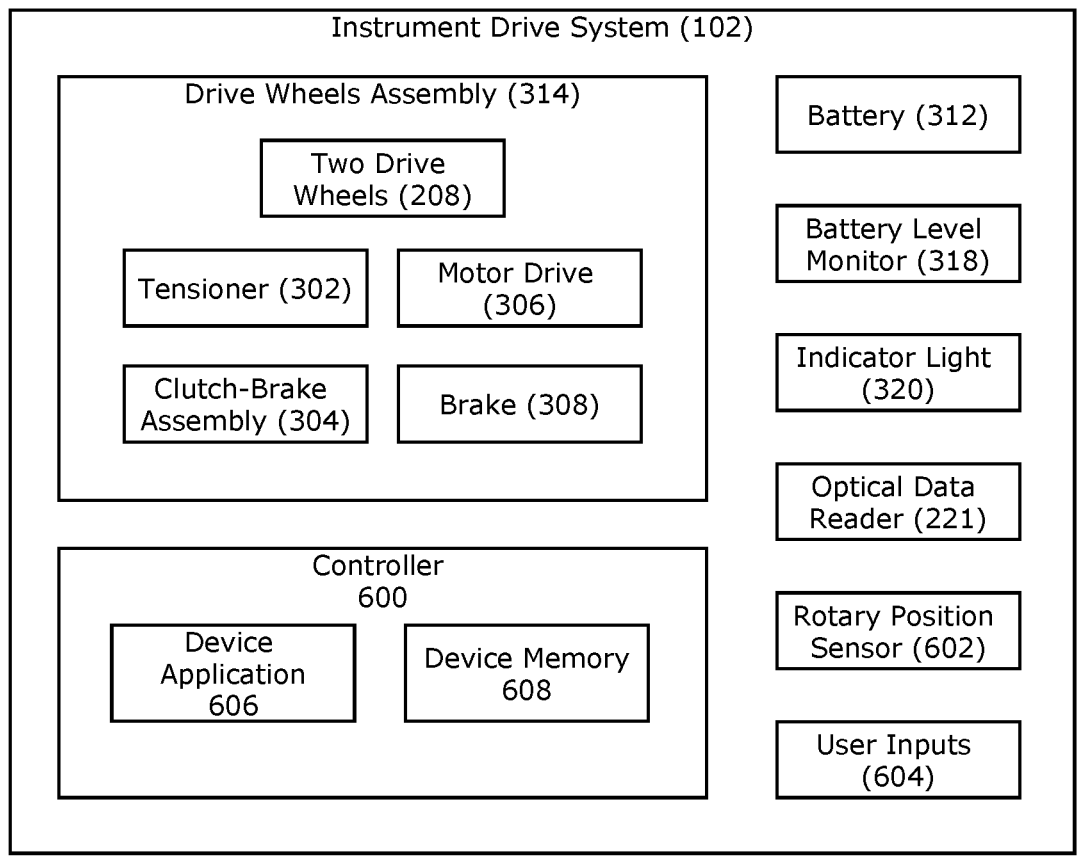
FIG. 6 illustrates a block diagram of said instrument drive system 102.

FIG. 6 illustrates a block diagram of said instrument drive system 102.

In one embodiment, said instrument drive system 102 can comprise a controller 600, a rotary position sensor 602 and a plurality of user inputs 604. Said controller 600 can comprise a device application 606 configured to monitor a status of said instrument 106, said two drive wheels 208, said motor drive 306 and said plurality of user inputs 604, and said rotary position sensor 602.

In one embodiment, said optical data reader 221 can be in data communication with said device application 606 of said controller 600. In one embodiment, said optical data reader 221 can be arranged within said working channel 210 and configured to read said plurality of machine-readable signatures 402 as said instrument 106 is moved in a forward and reverse direction.

In one embodiment, said instrument drive system 102 can comprise a sealed unit that can be co-processed with said endoscope assembly 104 for sterilization.

In one embodiment, said instrument drive system 102 can comprise said rotary position sensor 602. Said device application 606 of said controller 600 can monitor a signal from said rotary position sensor 602 indicating rotational speed of said two drive wheels 208.

In one embodiment, said charging and communication port 328 can connect to external appliance, such as a mobile phone, a charging cradle, a computer, etc., allowing to data stored in said device application 606 of said controller 600.

In one embodiment, said instrument drive system 102 can comprise said plurality of user inputs 604, such as said one or more direction buttons 316, said control knob 329 and further such as a variable speed input for adjusting a catheter feed speed, a PID, an RPM selector, a gear selector for adjusting gearing and torque settings of said two drive wheels 208.

In one embodiment, said instrument drive system 102 can be set up to insert a 48-inch catheter in approximately 2 seconds; wherein said two drive wheels 208 might be set up to advance 20 revolutions (assuming 0.75-inch diameter for the wheels, 0 slippage). Targeting 2 seconds for the advance, a 600 RPM setting might be required for said motor drive 306, in this hypothetical.

In one embodiment, said device application 606 can be programmed to alter a speed, direction or other setting of said two drive wheels 208 upon receiving a signal related to said plurality of machine-readable signatures 402.

For example when said instrument 106 has been substantially fed into said instrument drive system 102 such that said second optical signature 402b at said proximal end 404 has reached said two drive wheels 208 and said optical data reader 221 it can be known that said distal end 118 is reaching the end of said flexible shaft 116 and should be slowed down so as to not damage or injure a patient due to a puncture.

In one embodiment, said device application 606 of said controller 600 can cause said two drive wheels 208 to disengage or decouple or otherwise engage said clutch-brake assembly 304 and/or said brake 308 in order to slow/stop movement of said instrument 106.

In one embodiment, said device application 606 can be configured to reverse movement said two drive wheels 208 and therefore of said instrument 106 to protect users of said instrument drive system 102 or said instrument 106.

In one embodiment, said device application 606 of said controller 600 can be configured to stop or slow movement once said distal end 118 is near the objective.

In one embodiment, said first optical signature 402a and said second optical signature 402b can further contain groups of optical bands of varying lengths and spacings that can encode information about said instrument 106. For example, such information can include the length of said instrument 106 and the outer diameter of said shaft 206.

In one embodiment, said controller 600 can contain a device memory 608 that can store data associated with the use of said instrument drive system 102. Such data can include temperature, number of co-processing cycles, number of charging cycles of said battery 312, number of manipulations of said instrument 106, alarms and other data, as is known in the art.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

PARTS LIST said endoscope assembly 104,
Said instrument drive system 102,
Said instrument 106,
Said instrument channel 108,
Said inputs-line 110,
Said inputs-controls 112,
Said deflection control 114,
Said flexible shaft 116,
Said distal end 118,
Said optical viewer 120,
Said first instrument 202,
Said distal instrument 204,
Said shaft 206,
Said two drive wheels 208,
Said first drive wheel 208a,
Said second drive wheel 208b,
Said working channel 210,
Said optical data reader 221,
Said body 212,
Said drive gap 214,
Said female locking coupling 216,
Said male locking coupling 218,
Said port gasket 219,
Said shaft gasket 220,
Said cover 326,
Said adjustable tensioner 302,
Said clutch-brake assembly 304,
Said motor drive 306,
Said brake 308,
Said battery 312,
Said one or more direction buttons 316,
Said forward direction button 316a,
Said reverse direction button 316b,
Said control knob 329,
Said control axis 331,
Said one or more widths 310,
Said battery level monitor 318,
Said indicator display 320,
Said charging and communication port 328,
Said plurality of machine-readable signatures 402,
Said one or more meta data markers 408,
Said first optical signature 402a,
Said second optical signature 402b,
Said proximal end 404,
Said one or more distal markers 406,
Said controller 600,
Said rotary position sensor 602,
Said plurality of user inputs 604,
Said device application 606, and
said device memory 608.

Preferred Embodiment said instrument drive system 102 configured to attach to said instrument channel 108 of said endoscope assembly 104 and manage a relative feed position of said instrument 106 using said two drive wheels 208 and said device application 606 in said controller 600. Said instrument drive system 102 can be attached directly to said instrument channel 108 of said endoscope assembly 104. operation of said instrument drive system 102 can be proximate to said endoscope assembly 104 and said inputs-controls 112 and said deflection control 114 thereof.

Said instrument drive system 102 configured to attach to said instrument channel 108 of said endoscope assembly 104 and manage a relative feed position of said instrument 106 using said two drive wheels 208 and said device application 606 in said controller 600. Said instrument drive system 102 can be attached directly to said instrument channel 108 of said endoscope assembly 104. operation of said instrument drive system 102 can be proximate to said endoscope assembly 104 and said inputs-controls 112 and said deflection control 114 thereof.

Said instrument drive system 102 comprises said female locking coupling 216 for mounting to said male locking coupling 218 of said instrument channel 108. Said female locking coupling 216 comprises said port gasket 219 that can form a hermetic seal between said female locking coupling 216 and said male locking coupling 218 of said instrument channel 108. Said female locking coupling 216 comprises said shaft gasket 220 that can form a hermetic seal between said female locking coupling 216 and said shaft 206.

Said instrument drive system 102 configured to attach to said instrument channel 108 of said endoscope assembly 104 and manage a relative feed position of said instrument 106 using said two drive wheels 208 and said device application 606 in said controller 600. Said instrument drive system 102 can be configured to work in conjunction with said instrument 106 comprising said plurality of machine-readable signatures 402. Said instrument drive system 102 further comprises said optical data reader 221 configured to read a portion of said plurality of machine-readable signatures 402 as said instrument 106 can be feed into and removed from said instrument drive system 102. Said device application 606 can be configured to decode said plurality of machine-readable signatures 402 and thereby determine a relative feed position of said instrument 106 within said instrument drive system 102 and said endoscope assembly 104.

Said two drive wheels 208 can be in communication with said device application 606 and configured to feed said instrument 106 into and out of said instrument drive system 102 and said endoscope assembly 104 according to inputs from said device application 606 and said plurality of user inputs 604 of said instrument drive system 102. Said two drive wheels 208 can be arranged around said working channel 210. Said instrument 106 can be configured to be inserted into said instrument drive system 102 and through said working channel 210.

Said two drive wheels 208 can be removeable, rechargeable and adjustable.

Said two drive wheels 208 can be located inside of said body 212 and under said cover 326. Said cover 326 can be clear to monitor the status of said shaft 206, said two drive wheels 208, said working channel 210, and said drive gap 214. Said cover 326 can be removeable to address any issues within said body 212.

Said two drive wheels 208 comprises said adjustable tensioner 302 to allow for fine tuning of instrumentation feed speed, and said clutch-brake assembly 304 which can allow for decoupling of said motor drive 306 and said brake 308.

Said working channel 210 comprises said drive gap 214 being adjustable to said one or more widths 310 to accommodate different diameters for said instrument 106.

Said plurality of machine-readable signatures 402 comprises a foil band or other optically unique signature at both ends of said instrument 106.

Said plurality of machine-readable signatures 402 comprises said one or more meta data markers 408 such said first optical signature 402*a* at said distal end 118 of said instrument 106 and said second optical signature 402*b* at said proximal end 404 of said instrument 106. Said one or more distal markers 406 can be arranged along a portion of said instrument 106 to illustrate a relative location along said instrument 106. Said optical data reader 221 can be in data communication with said device application 606 of said controller 600. Said instrument drive system 102 can be configured to read said plurality of machine-readable signatures 402 using said optical data reader 221.

Said one or more distal markers 406 can be at predetermined distances from one another.

a portion of said one or more meta data markers 408 can disclose a total length, a diameter, a rigidity of said instrument 106.

Said optical data reader 221 can be arranged within said working channel 210 and configured to read said plurality of machine-readable signatures 402 as said instrument 106 can be moved in a forward and reverse direction.

Said device application 606 can be programmed to alter a speed, direction or other setting of said two drive wheels 208 upon receiving a signal related to said plurality of machine-readable signatures 402. wherein, when said instrument 106 has been substantially fed into said instrument drive system 102 such that said second optical signature 402*b* at said proximal end 404 has reached said two drive wheels 208 and said optical data reader 221 it can be known that said distal end 118 can be reaching the end of said flexible shaft 116 and should be slowed down so as to not damage or injure a patient due to a puncture.

Said controller 600 can be configured to stop or slow movement once said distal end 118 can be near the objective.

Said optical data reader 221 can be arranged within said working channel 210 and configured to read said plurality of machine-readable signatures 402 as said instrument 106 can be moved in a forward and reverse direction.

Said instrument drive system 102 comprises said rotary position sensor 602. Said controller 600 can monitor a signal from said rotary position sensor 602 indicating rotational speed of said two drive wheels 208.

Said device application 606 can be configured to reverse movement said two drive wheels 208 and therefore of said instrument 106 to protect users of said instrument drive system 102 or said instrument 106.

Said controller 600 can be configured to stop or slow movement once said distal end 118 can be near the objective.

The invention claimed is:

1. An instrument drive system configured to manage a relative feed position of an instrument in an instrument channel of an endoscope assembly and manage a relative feed position of said instrument, wherein said instrument drive system comprises:
   two drive wheels, a working channel, a device application, and a controller;
   said controller comprises a device memory containing said device application;
   said two drive wheels are arranged around said working channel within said instrument drive system;

said instrument drive system is configured to work in conjunction with said instrument comprising a plurality of machine-readable signatures;

said instrument drive system further comprises an optical data reader configured to read a portion of said plurality of machine-readable signatures as said instrument is feed into and removed from said instrument drive system;

said device application is configured to decode said plurality of machine-readable signatures and thereby determine a relative feed position of said instrument within said instrument drive system and said endoscope assembly;

said two drive wheels are in communication with said device application;

said device application is configured to feed said instrument into and out of said instrument drive system and said endoscope assembly according to inputs from said device application and a plurality of user inputs of said instrument drive system;

said instrument is configured to be inserted into said instrument drive system and through said working channel; and said two drive wheels comprise an adjustable tensioner to allow for fine tuning of instrumentation feed speed, and a clutch-brake assembly which can allow for decoupling of a motor drive and a brake.

2. The instrument drive system of claim 1, wherein:
said two drive wheels are located inside of a body and under a cover;
said cover is clear to monitor the status of a shaft, said two drive wheels, said working channel, and a drive gap; and
said cover is removeable to address any issues within said body.

3. The instrument drive system of claim 1, wherein:
said working channel comprises a drive gap being adjustable to one or more widths to accommodate different diameters for said instrument.

4. The instrument drive system of claim 1, wherein:
said plurality of machine-readable signatures comprises a foil band or other optically unique signature at both ends of said instrument.

5. The instrument drive system of claim 1, wherein:
said plurality of machine-readable signatures comprises one or more meta data markers such a first optical signature at a distal end of said instrument and a second optical signature at a proximal end of said instrument;
one or more distal markers are arranged along a portion of said instrument to illustrate a relative location along said instrument;
said optical data reader is in data communication with said device application; and
said instrument drive system is configured to read said plurality of machine-readable signatures using said optical data reader.

6. The instrument drive system of claim 5, wherein:
said one or more distal markers is at pre-determined distances from one another.

7. The instrument drive system of claim 5, wherein:
said optical data reader is arranged within said working channel and configured to read said plurality of machine-readable signatures as said instrument is moved in a forward and reverse direction.

8. The instrument drive system of claim 5, wherein:
said device application is programmed to alter a speed, direction or other setting of said two drive wheels upon receiving a signal related to said plurality of machine-readable signatures; and
said device application is configured for
determining when said second optical signature at said proximal end has reached said two drive wheels and said optical data reader, and
slowing said instrument since it is reaching said device application the end of a flexible shaft to minimize damage to said instrument and injury to a patient due to a puncture.

9. The instrument drive system of claim 5, wherein:
said device application is configured to stop or slow movement once said distal end is near an objective.

10. The instrument drive system of claim 1, wherein:
said optical data reader is arranged within said working channel and configured to read said plurality of machine-readable signatures as said instrument is moved in a forward and reverse direction.

11. The instrument drive system of claim 1, wherein:
said instrument drive system comprises a rotary position sensor; and
said device application is configured to monitor a signal from said rotary position sensor indicating rotational speed of said two drive wheels.

12. The instrument drive system of claim 1, wherein:
said device application is configured to reverse movement said two drive wheels and therefore of said instrument to protect users of said instrument drive system or said instrument.

13. The instrument drive system of claim 1, wherein:
said device application is configured to stop or slow movement once said distal end is near an objective.

14. The instrument drive system of claim 1, wherein:
said controller comprises a device memory that stores data associated with the use of said instrument drive system; and
such data includes temperature, number of co-processing cycles, number of charging cycles of a battery, number of manipulations of said instrument, alarms and other data.

* * * * *